(12) United States Patent
Hill et al.

(10) Patent No.: US 8,084,667 B2
(45) Date of Patent: Dec. 27, 2011

(54) METHOD OF MODIFYING PLANT PHENOTYPES WITH NONSYMBIOTIC HEMOGLOBIN

(75) Inventors: Robert D. Hill, Winnipeg (CA); Kevin Baron, Carberry (CA)

(73) Assignee: The University of Manitoba, Winnipeg, Manitoba (CA)

( * ) Notice: Subject to any disclaimer, the term of this patent is extended or adjusted under 35 U.S.C. 154(b) by 1197 days.

(21) Appl. No.: 10/582,321

(22) PCT Filed: Dec. 10, 2004

(86) PCT No.: PCT/IB2004/004419
§ 371 (c)(1),
(2), (4) Date: May 22, 2007

(87) PCT Pub. No.: WO2005/055703
PCT Pub. Date: Jun. 23, 2005

(65) Prior Publication Data
US 2007/0256196 A1 Nov. 1, 2007

Related U.S. Application Data

(60) Provisional application No. 60/528,777, filed on Dec. 12, 2003.

(51) Int. Cl.
*C12N 15/82* (2006.01)
*A01H 5/00* (2006.01)
(52) U.S. Cl. ......... 800/286; 800/282; 800/285; 800/290
(58) Field of Classification Search .................. None
See application file for complete search history.

(56) References Cited

U.S. PATENT DOCUMENTS

| 5,959,187 A | 9/1999 | Bailey et al. |
| 6,372,961 B1 | 4/2002 | Tarczynski et al. |
| 6,936,749 B1 | 8/2005 | Guy et al. |

FOREIGN PATENT DOCUMENTS

| WO | WO 98/12913 | | 4/1998 |
| WO | WO-99/02687 | | 1/1999 |
| WO | WO 00/00597 | * | 1/2000 |
| WO | WO-2004/057946 A2 | | 7/2004 |
| WO | WO-2004/057946 A3 | | 7/2004 |
| WO | WO 2004/087755 A2 | | 10/2004 |

OTHER PUBLICATIONS

Dordas et al. Expression of a stress-induced hemoglobin affects NO levels produced by alfalfa root cultures under hypoxic stress. (2003) The Plant Journal; vol. 35; pp. 763-770.*
Sowa et al. Altering hemoglobin levels changes energy status in maize cells under hypoxia. (1998) PNAS; vol. 95; pp. 10317-10321.*
Arredondo-Peter et al. Plant Hemoglobins (1998) Plant Physiol.; vol. 118; pp. 1121-1125.*
Elomaa et al. Transformation of antisense constructs of the chalcone synthase gene superfamily into Gerber hybrida: differential effect on the expression of family members. (1996) Molecular Breeding, vol. 2, pp. 41-50.*
Colliver et al. Differential modification of flavonoid and isoflavonoid biosynthesis with an antisense chalcone synthase construct in transgenic *Lotus corniculatus*. (1997) PMB; vol. 35; pp. 509-522.*
Dolferus R. et al., "Strategies of Gene Action in *Arabidopisis* during Hypoxia," *Annals of Botany*, vol. 79, (Supplement A); pp. 21-31, 1997.
Goodenough U., Chapter 19, "Population Geneitcs 1," *Genetics*, 2nd ed., Holt, Rinehart and Winston; pp. 771-772, 1978.
Dordas C. et al., "Plant Haemoglobins, Nitric Oxide and Hypoxic Stress," *Annals of Botany*, vol. 91; pp. 173-178, 2003.
Andersson et al., "A new hemoglobin gene from soybean: A role for hemoglobin in all plants," *Proc. Natl. Acad. Sci. USA.*, vol. 93, pp. 5682-5687, 1996.
Jacobsen-Lyon et al., "Symbiotic and nonsymbiotic haemoglobin genes of *Casuarina glauca*," *The Plant Cell*, vol. 7:213-223, 1995.
Sowa et al., "Altering hemoglobin levels changes energy status in maize cells under hypoxia," *Proc. Natl. Acad. Sci. USA*, vol. 95, pp. 10317-10321, 1998.
Arredondo-Peter et al., "Gene Cloning, Analysis, and O2-Binding Kinetics of a Recombianant Protein Synthesized in *Escherichia coli*," *Plant Physiology*, vol. 115, pp. 1259-1266, 1997.
Taylor et al., "A cereal haemoglobin gene is expressed in seed and root tissues under anaerobic conditions", *Plant Molecular Biology*, vol. 24: 853-862, 1994.
Duff et al., "Expression, Purification, and Properties of Recombinant Barley (*Hordeum* sp.) Hemoglobin," *Journal of Biological Chemistry*, vol. 272, No. 27, 16746-16752, 1997.
Trevaskis et al., "Two hemoglobin genes in *Arabidopsis thaliana*: The evolutionary origins of leghemoglobins," *Proc. Natl. Acad. Sci. USA*, vol. 94, pp. 12230-12234, 1997.
Heckmann; "A single hemoglobin gene in *Myrica gale* retains both symbiotic and non-symbiotic specificity", *Plant Mol Biol* (2006) 61:769-779.
Hebelstrup et al.; "Expression of NO scavenging hemoglobin is involved in the timing of bolting in *Arabidopsis thaliana*", Planta (2008) 227:917-927.
He et al.; "Nitric Oxide Represses the *Arabidopsis* Floral Transition", www.sciencemag.org, (Sep. 24, 2004), vol. 305, Science.
Hebelstrup et al.; "Hemoglobin is essential for normal growth of *Arabidopsis* organs"; Physiologia Plantarum; (2006) 127:157-166.
Holmberg et al., "Transgenic Tobacco Expressing Vitreoscilla Hemoglobin Exhibits Enhanced Growth and Altered Metabolite Production", *Nature Biotechnology*, vol. 15, 1997, pp. 244-247.
Hunt et al., "Increased Level of Hemoglobin 1 Enhances Survival of Hypoxic Stress and Promotes Early Growth in *Arabidopsis thaliana*", *Proc. Natl. Acad. Sci. USA*, vol. 99, No. 26, 2002, pp. 17197-17202.
Igamberdiev et al., "NADH-Dependent Metabolism of Nitric Oxide in Alfalfa Root Cultures Expressing Barley hemoglobin", *Planta*, vol. 219, 2004, pp. 95-102.
Seregelyes Csaba et al. "Phytoglobins can interfere with nitric oxide functions during plant growth and pathogenic responses: A transgenic approach." Plant Science (Oxford), vol. 165, No. 3, Sep. 2003, pp. 541-550.

(Continued)

*Primary Examiner* — Cathy Kingdon Worley
(74) *Attorney, Agent, or Firm* — Foley & Lardner LLP

(57) ABSTRACT

The present invention provides a method of modifying a plant phenotype by transforming a plant to alter the level of expression of non-symbiotic plant hemoglobin in the plant, whereby the transformed plant exhibits, under normal oxygen conditions, a plant phenotype that is modified as compared to a non-transformed plant. Plants exhibiting modified phenotypes under normal oxygen conditions also are provided. Methods of modifying the response to a plant hormone in a plant also are provided.

7 Claims, 6 Drawing Sheets

OTHER PUBLICATIONS

Dordas C. et al. "Expression of a stress-induced hemoglobin affects NO levels produced by alfalfa root cultures under hypoxic stress" Plant Journal, Blackwell Scientific Publications, Oxford, GB, vol. 35, Sep. 2003, pp. 763-770.

Häggman, H. et al.: "Expression of Vitreoscilla haemoglobin in hybrid aspen (*Populus tremula x tremuloides*)" Plant Biology Journal, vol. 1, Jul. 2003, pp. 287-300.

Hebelstrup Kim H. et al.: "Metabolic effects of hemoglobin gene expression in plants" Gene (Amsterdam), vol. 398, No. 1-2, Sp. Iss. SI, Aug. 2007, pp. 86-93.

Taylor et al., "A cerial haemoglobin gene is expressed in seed and root tissues under anaerobic conditions," Plant Molecular Biology, vol. 24, pp. 853-862, 1994.

Andersson et al., "A new hemoglobin gene from soybean: A role for hemoglobin in all plants," Proc. Natl. Acad. Sci., vol. 93, pp. 5682-5687, Jun. 1996.

Trevaskis et al., "Two hemoglobin genes in *Arabidopsis thaliana*: The evolutionary origins of leghemoglobins," Proc. Natl. Acad. Sci., vol. 94, pp. 12230-12234, Oct. 1997.

Mallory et al., "MicroRNA-directed regulation: to cleave or not to cleave," Trends in Plant Science, vol. 13, No. 7, pp. 359-367, 2008.

Karginov et al., "A biochemical approach to identifying microRNA targets," PNAS, vol. 104, No. 49, pp. 19291-19296, Dec. 4, 2007.

\* cited by examiner

FIGURE 1

METHOD OF MODIFYING PLANT PHENOTYPES WITH NONSYMBIOTIC HEMOGLOBIN

CROSS-REFERENCE TO RELATED PATENT APPLICATIONS

This application is the National Phase of PCT/IB2004/004419, filed Dec. 10, 2004, and published as WO 2005/055703 on Jun. 23, 2005, which claims priority to U.S. Provisional Patent Application No. 60/528,777, filed on Dec. 12, 2003, the entirety of these applications is incorporated herein by reference.

BACKGROUND OF THE INVENTION

The present invention relates generally to the field of agriculture.

Hemoglobins are widespread throughout the biosphere. (See Wittenberg and Wittenberg, 1990, *Ann. Rev Biophys Chem.* 19:217-241). They are found in a broad range of organisms from bacteria, through unicellular eukaryotes, to plants and animals, suggesting that they predate divergence of life into plant and animal forms.

Plant hemoglobins have been classified into symbiotic and nonsymbiotic types (Appleby, 1992, *Sci Progress* 76:65-398). Symbiotic hemoglobins are found in plants that are capable of participating in microbial symbioses, where they function in regulating oxygen supply to nitrogen fixing bacteria. Nonsymbiotic hemoglobins were discovered recently and are thought to be the evolutionary predecessors of the more specialized symbiotic leghemoglobins. The ubiquitous nature of nonsymbiotic hemoglobins is evidenced by their broad presence across the plant kingdom. (See Appleby, 1985, *Nitrogen Fixation and $CO_2$ Metabolism*, eds. Ludden and Burris, pp. 41-51).

The widespread presence and long evolutionary history of plant hemoglobins suggest a major role for them in the life of plants. Nonsymbiotic plant hemoglobins (nsHb), consisting of class 1, class 2, and truncated Hbs (class 3) are believed to be expressed universally in members of the plant kingdom. (Andersson et al, 1996, *Proc Natl Acad Sci* 93: 5682-5687; Watts et al, 2001, *PNAS* 98: 10119-10124).

The existence of plant hemoglobins in the root nodules of legumes for almost has been known for almost 60 years. (See, e.g., Kubo, 1939, *Acta Phitochem* 11:195-200; Keilen and Wang, 1945, *Nature* 155:227-229). Over the years, hemoglobins have been positively identified in three non-leguminous dicotyledonous plants: *Parasponia andersonii, Tream tomentosa,* and *Casuarina glauce*. (See, e.g., Appleby et al., 1983, *Science* 220:951-954; Bogusz et al., 1988, *Nature* 331:178-180; Kortt et al., 1988, *FEBS Lett* 180:55-60). Recently, an Hb cDNA from barley was isolated and the gene was demonstrated to be expressed in seed and root tissues under anaerobic conditions. (See Taylor et al., 1984, *Plant Mol Biol* 24:853-882). These observations support the viewpoint that plant hemoglobins have a common origin. (See Landsmann et al., 1986, *Nature* 324:166-168). Since Hb has been demonstrated to occur in two of the major divisions of the plant kingdom, it is likely that an Hb gene is present in the genome of all higher plants. (See Brown et al., 1984, *J Mol Evol* 21:19-32; Bogusz et al., 1988; Appleby, 1992, *Sci Progress* 76:365-398; Taylor et al., 1994, *Plant Mol Biol* 24: 853-862; Andersson et al., 1996, *Proc Natl Acad Sci USA* 93:427431; Hardison, 1996, *Proc Natl Acad Sci USA* 93:5675-5682).

The reported lack of effect of hemoglobin on cell growth and oxygen uptake under normal air conditions likely reflects the fact that barley (See Taylor et al., 1994, *Plant Mol Biol* 24: 853-862) and maize hemoglobin genes are induced under conditions of limited oxygen availability, resulting in the protein having little effect when oxygen supplies are not impaired. It has been shown clearly that the energy status of maize cells when oxygen is limiting is affected by the ability of the cells to produce hemoglobin. Total adenylates and ATP levels are maintained during the period of exposure to limiting oxygen when hemoglobin is constitutively expressed in the cells. (See WO 00/00597). Alternatively, when hemoglobin expression was suppressed by constitutive expression of antisense barley hemoglobin message, the cells were unable to maintain their energy status during oxygen limitation.

Class 1 nonsymbiotic hemoglobins are present in seed, root and stem tissue of monocots and dicots where they are expressed in response to hypoxia, etiolation, sucrose/mannitol addition, cytokinin, ARR1 or auxin (IAA) treatments in addition to nutrient oversupply ($NO_3^-$, $NO_2^-$ and NO) and deprivation (P, K, and Fe). (See Taylor et al., 1994, *Plant Mol Biol* 24: 853-862; Hunt et al, 2001, *Plant Mol Biol* 47: 677-692; Lira-Ruan et al, 2001, *Plant Sci* 161: 279-287; Kim et al., 2003, *Journal of Plant Biology* 46: 161-166; Ohwaki et al., 2003, *Plant and Cell Physiology* 44: S78; Ross et al, 2004, *J Exp Bot* 55: 1721-1731; Wang et al, 2003, *Plant Cell Environ* 26: 673-680; Dordas et al, 2003, *Plant Journal* 35: 763-770). Class 1 nsHbs are also known to be repressed in roots following infection by mycorrhizal fungi. (See Uchiumi et al, 2002, *Plant Cell Physiol* 43: 1351-1358).

Hunt et al., 2002, *PNAS* 99: 17197-202, reported that *A. thaliana* over-expressing a class 1 *A. thaliana* nsHb (GLB1-high affinity) showed improved survival following severe hypoxic stress, and that similar *A. thaliana* plants transformed to over-express *Parasponia* class 1 Hb (GLB1S-medium affinity) demonstrated an intermediate level of hypoxic protection relative to controls and to plants transformed with GLB1 mutated to have a low affinity for gaseous ligands (GLB1 (HE7L)-low affinity).

More recent work with transgenic maize cell suspensions (Dordas et al, 2004, *Planta* 219: 66-72), alfalfa root cultures (Dordas et al, 2003, *Plant Journal* 35: 763-770; Igamberdiev et al, 2004, *Planta* 219: 95-102) and *A. thaliana* plants (Perazzolli et al, 2004, *Plant Cell* 16: 2785-2794) has demonstrated that class 1 nsHbs modulate plant NO levels, both in vitro and in vivo, with NO levels being inversely related to class 1 nsHb expression. Both barley and alfalfa class 1 nsHbs, together with a corresponding reductase, have been shown to metabolize NO to $NO_3^-$, with such activity being NAD(P)H-dependent and displaying characteristics of a NO-dioxygenase. (See Igamberdiev et al., supra; Seregelyes et al, 2004, *FEBS Lett* 571: 61-66).

Transgenic tobacco (*Nicotiana tabacum*) plants expressing a hypoxia-inducible bacterial hemoglobin (VHb) from the obligate aerobic, gram-negative bacteria *Vitreoscilla* have been shown to exhibit reduced emergence time, enhanced growth, accelerated development and increased chlorophyll content relative to control plants (Holmberg et al. 1997, *Nature Biotechnol* 15: 244-247). Petunias (*Petunia hybrida*) and tobacco plants expressing VHb also have demonstrated improved hydroponic growth and waterlogging tolerance relative to control plants. (See Mao et al. 2003, *Acta Botanica Sinica* 45: 205-210). VHb is a bacterial hemoglobin, and is separate and distinct from the plant nonsymbiotic hemoglobins encompassed by the present invention. For example, VHb has different biochemical properties than nsHb, has different ligand-binding properties, and has a lower oxygen affinity.

Hunt et al., 2002, supra, reported that that GLB1-transformed plants exhibited increased early growth (i.e., at 14 days), greater root and shoot weight at 14 days, and had longer roots with a lower root hair density and more lateral roots than control plants, when the transformed plants were grown under normal oxygen conditions. However, no altered development rate of leaf production was observed. Additionally, Hunt et al. found no differences in morphological development of *A. thaliana* plants expressing either *Arabidopsis* or *Parasponia* class 1 nsHb. The authors hypothesized that, although the plant was grown under normoxic conditions, the plant may have experienced localized, transient hypoxia, noting that a transient hypoxic phase may be experienced during germination. They therefore associated the observed effects on early root growth as being due to the transformed plant's improved ability to withstand that hypoxia.

While the effects of nonsymbiotic hemoglobin on oxygen uptake, NO levels, and survival under hypoxic conditions have been studied, the ability to modify plant phenotypes or mineral nutrition under normal oxygen conditions by controlling levels of nonsymbiotic hemoglobin has not heretofore been determined. Indeed, conflicting reports exist as to the influence of class 1 nsHb and/or VHb expression on plant growth under non-stressed, as compared to stressed, conditions. (See, e.g., Seregelyes et al. 2004, *Febs Letters* 571: 61-66; Haggman et al. 2003, *Plant Biotechnology Journal* 1: 287-300; Frey et al. 2004; Perazzolli et al. 2004, *Plant Cell* 16: 2785-2794).

There are a number of different plant phenotypes that it would be useful to be able to modify. For example, apical dominance in shoots and roots, taproot width, leaf size, leaf length, petiole length, internode length, plant shape, erect versus prostrate growing habit, flower color, early versus late flowering, chlorophyll content, and nutrient uptake, concentration, or metabolism.

SUMMARY

According to a first aspect of the invention, there is provided a method of modifying one or more plant phenotypes by altering the level of non-symbiotic hemoglobin (nsHb) expression in the plant. In one embodiment, the method comprises transforming a plant to alter the level of expression of non-symbiotic plant hemoglobin in the plant as compared to a non-transformed plant that is not transformed to alter the level of expression of non-symbiotic plant hemoglobin, thereby yielding a transformed plant, wherein said transformed plant exhibits, under normal oxygen conditions, a plant phenotype that is modified as compared to said non-transformed plant.

In embodiments where the phenotype is a root phenotype, the modified phenotype is selected from the group consisting of apical dominance and taproot width. In other embodiments, the phenotype is selected from the group consisting of shoot or root apical dominance, taproot width, leaf size, leaf length, plant shape, erect versus prostrate growing habit, flower color, early versus late flowering, chlorophyll content, and combinations thereof. In further embodiments, the plant phenotype is a plant growth characteristic selected from the group consisting of cell-cycle initiation, cell differentiation, cell elongation, time to reproductive maturity, time from vegetative to reproductive development, and combinations thereof. In additional embodiments, the plant phenotype is a plant characteristic selected from the group consisting of vegetative growth and yield. In other embodiments the plant phenotype is the relative proportions of one or more plant components selected from the group consisting of leaf, stem, and reproductive tissue. Additional embodiments include those where the plant phenotype is the plant's uptake, concentration or metabolism of nutrients.

In some embodiments, the transformed plant exhibits an increased level of expression of non-symbiotic hemoglobin as compared to said non-transformed plant. Those embodiments may comprise transforming the plant with an expression system comprising a nucleic acid molecule encoding a plant nonsymbiotic hemoglobin. In other embodiments, the transformed plant exhibits a decreased level of expression of non-symbiotic hemoglobin as compared to said non-transformed plant. Those embodiments may comprise transforming the plant with an expression system comprising an antisense plant nonsymbiotic hemoglobin nucleic acid molecule.

In accordance with another aspect, the invention provides plants transformed in accordance with these methods, exhibiting a modified phenotype under normal oxygen conditions as compared to a non-transformed plant that is not transformed to alter the level of expression of non-symbiotic plant hemoglobin. In some embodiments, the plant exhibits an increased level of expression of non-symbiotic hemoglobin as compared to said non-transformed plant. In other embodiments, the plant exhibits a decreased level of expression of non-symbiotic hemoglobin as compared to said non-transformed plant.

In accordance with another aspect, the invention provides a method of modifying the response to a plant hormone in a plant, comprising transforming a plant to alter the level of expression of non-symbiotic plant hemoglobin in the plant as compared to a non-transformed plant that is not transformed to alter the level of expression of non-symbiotic plant hemoglobin, thereby yielding transformed plant, wherein said transformed plant exhibits, under normal oxygen conditions, an altered response to a plant hormone as compared to said non-transformed plant. In one embodiment, the altered plant hormone response is a response to a hormone selected from the group consisting of gibberellins, auxins, cytokinins, ABA, brassinosteroids and ethylene. In another embodiment, the transformed plant exhibits an increased response to a plant hormone as compared to said non-transformed plant.

These and other aspects of the invention are described in more detail below, and are illustrated in the examples.

BRIEF DESCRIPTION OF THE DRAWINGS

FIG. 1 sets forth data on four transformed alfalfa plant lines at 14, 21, 28, 35 and 63 days after transplantation.

DESCRIPTION

Figure 2:
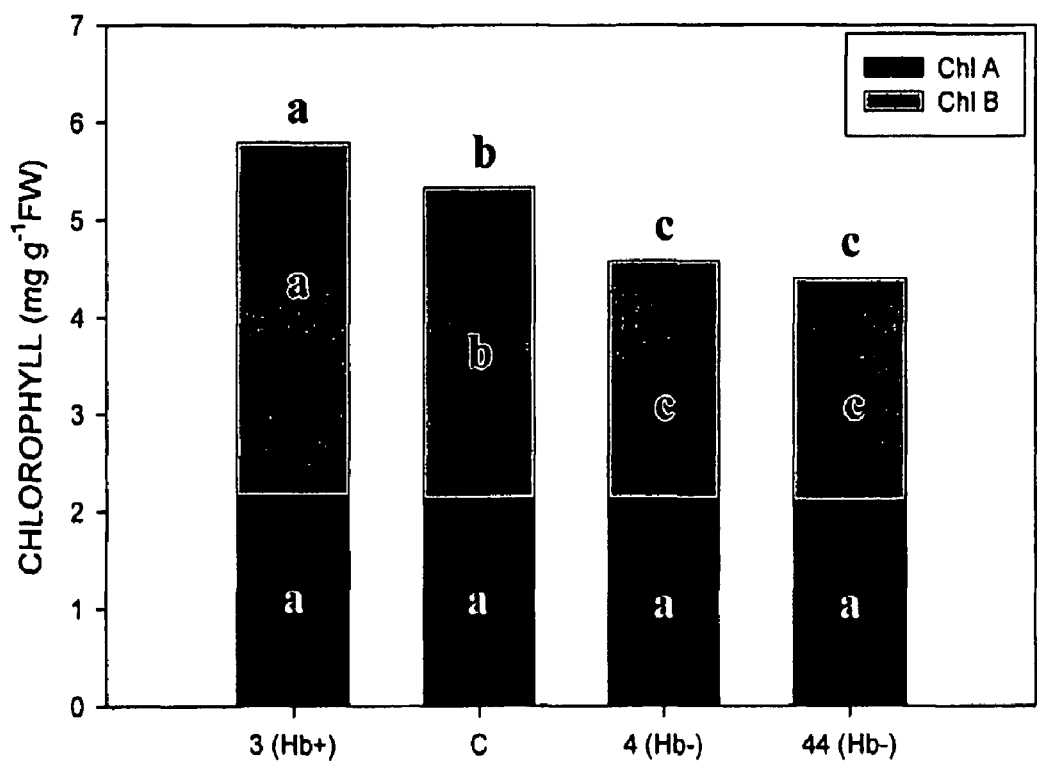
FIG. 2 shows the chlorophyll content of four transformed alfalfa lines.

Described herein are methods of modifying one or more plant phenotypes by altering the level of non-symbiotic hemoglobin (nsHb) expression in the plant. In one aspect, the methods comprise modifying a plant to over-express nsHb, such that the plant exhibits an increased level of nsHb (Hb+) relative to a plant that has not been transformed. In another aspect, the methods comprise modifying a plant to under-express nsHb, such that the plant exhibits a decreased level of nsHb (Hb−) relative to a plant that has not been transformed. In another aspect, only one part of the plant is modified to over-express or under-express nsHb. In another aspect, different parts of the plant (such as the roots, shoots, stems, leaves, or reproductive cells) are independently modified to over-express or under-express nsHb.

The modification can be achieved through standard recombinant technologies. For example, a suitable expression cassette can be integrated into the plant genome. Alternatively, the plant can be transfected with a suitable expression vector. In one aspect, the expression system (such as the expression cassette or expression vector) comprises a promoter, such as a plant promoter or an inducible or repressible promoter. The use of an inducible or repressible promoter permits selective activation of the nucleotide sequence comprised in the expression vector, so that overexpression or repression of nsHb can be regulated.

In embodiments where over-expression of nsHb is desired, the expression system comprises a nucleotide sequence encoding a plant nsHb. In embodiments where under expression (or repression of nsHb expression) of nsHb is desired, the expression system comprises an antisense nsHb nucleotide sequence, such as an antisense copy of the target plant's nsHb gene.

The invention includes the use of any nucleotide sequence encoding a plant nsHb, and the use of antisense sequences thereto. A number of plant nsHb genes have been published. For example, Taylor et al., *Plant Mol Biol* 24: 853-62 (1994), discloses a barley ns-Hb nucleotide sequence; Arrendondo-Peter, *Plant Physiol.* 115: 1259-66 (1997) discloses a rice ns-Hb sequence; Trevaskis et al., *Proc. Nat'l Acad. Sci. USA* 94: 12230-34 (1997) describes an *Arabidopsis* ns-Hb sequence; Andersson et al., *Proc. Nat'l Acad. Sci. USA* 93: 5682-87 (1996) describes a soybean ns-Hb sequence; Jacobsen-Lyon et al., *Plant Cell* 7: 213-23 (1995), describes an ns-Hb from *Casuarina glauca*. Nonsymbiotic hemoglobin sequences also have been reported for other plants, including *Cichorium* (Hendriks et al., *Biochim. Biophys. Acta.* 1443: 193-97 (1998), *Lotus japonica* (Uchiumi et al., *Plant Cell Physiol.* 43: 1351-58 (2002)), wheat and potato (Larsen, *Biochim. Biophys. Acta.* 1621: 299-305 (2003)), and *Euryale ferox* (Guldner et al., *J. Evol. Biol.* 17: 48-54 (2004)).

Other methods of achieving over- or under-expression of nsHb also may be used. For example, there are conventional techniques that employ a promoter or repressor to induce or repress expression, respectively, of the plant's nsHb genes.

The expression system may further comprise other components known in the art, such as one or more promoters and one or more selectable markers. In one embodiment, the expression system comprises a strong constitutive promoter. In another embodiment, the expression system comprises a tissue-specific promoter.

In some circumstances, it is advantageous to control expression of the expression cassette or vector at selected points during the plant's life cycle, so as to achieve over-expression or under expression of nsHb at selected time points. This can be achieved by using an expression cassette or vector comprising an inducible or repressible promoter, and by inducing or repressing expression at selected points in the plant's life cycle to achieve the desired effect. Chemical-inducible systems for regulated expression of plant genes are known. See, e.g., Zuo J. & Chua N H, 2000, *Curr. Opin. Biotechnol.* 11: 146-51. The use of such systems is encompassed by the present invention.

In some circumstances, it is advantageous to effect targeted expression of the expression cassette or vector, so as to achieve over-expression or under expression of nsHb in specific cells, such as root, shoot, stem, leaf or reproductive cells. This can be effected by methods known in the art. For example, the expression cassette or vector may comprise a tissue-specific promoter, such as a root- or shoot-specific promoter. Suitable such promoters are known. See, e.g., Zhang J Z, 2003, *Curr Opin Plant Biol* 6: 430-440. Alternatively, the expression cassette or vector can be targeted to the target cells, such as, for example, by targeted gene delivery or by direct administration to the target cells.

Any plant can be modified in accordance with the present invention. Exemplary plants include decorative plants such as flowering plants and grasses, forage plants, maize, barley, wheat, wild oat and *Echinochloa crus galli*.

Plant phenotypes that can be altered in accordance with the invention include apical dominance in shoots and roots, taproot width, leaf size, leaf length, petiole length, internode length, plant shape, erect versus prostrate growing habit, flower color, early versus late flowering, chlorophyll content, and nutrient uptake, concentration or metabolism.

For example, nsHb+ plants may exhibit greater apical dominance in shoots, such that the shoots are longer with less branching than shoots of a non-transformed plant. Likewise, nsHb+ plants may exhibit greater apical dominance in roots, such that the roots are longer with less branching than roots of a non-transformed plant. See FIGS. 8 & 9. Such nsHb+ plants also may exhibit thicker taproots. See FIG. 8. These results are not expected from Hunt et al., supra, which did not report any effect of Hb over-expression on root apical dominance or on taproot width.

Plants transformed to over-express nsHb may exhibit an erect growing habit compared to non-transformed plants, while nsHb− plants may exhibit a prostrate growing habit. nsHb+ plants may exhibit earlier flowering than non-transformed plants, while nsHb− plants may exhibit later flowering. nsHb+ plants may exhibit higher chlorophyll content, while nsHb− plants may exhibit a lower chlorophyll content.

Plants modified to over-express nsHb may exhibit increased mean internode length and increased area per leaflet. Such nsHb+ plants also may exhibit elongated and needled leaflets with longer petioles and petiolules. Conversely, plants modified to under-express nsHb may exhibit decreased mean internode length and decreased area per leaflet, with oval leaflets. nsHb− plants also may exhibit more stems per plant, more nodes per stem, and more leaflets per plant. (Thus, in nsHb− plants, reduced area per leaflet may be compensated by an increased number of trifoliates per plant, stems per plant and nodes per stem.) In contrast, nsHb+ plants may exhibit thicker stems with elevated specific stem weights.

For example, nsHb+ plants may exhibit such phenotypes as oblanceolate leaflets, elongated petioles, petiolules and internodes, elevated shoot:root ratios, reduced leaf:stem ratios, longer stems and an erect growth habit with little or no tillering relative to control plants. Relative to control plants, nsHb− plants may exhibit compressed oval leaflets, shorter petioles, petiolules and internodes, release of axillary buds, more shoots per plant (tillering), more nodes per stem, and a prostrate growth habit.

The invention also provides a method for controlling plant growth, such as, for example, controlling cell-cycle-related processes (i.e., initiation, differentiation and elongation), rate of development (i.e., time to reproductive maturity, transition from vegetative to reproductive development). Generally, plants modified to over-express nsHb exhibit enhanced (i.e., earlier) growth characteristics than non-transformed plants. Conversely, plants modified to under-express nsHb exhibit reduced (i.e., delayed) growth characteristics than non-transformed plants.

For example, the present inventors have found that nsHb+ plants according to the invention flower before control and nsHb− plants. Although a similar pattern was observed in transgenic tobacco plants expressing VHb (see Holmberg et al. 1997, supra), Hunt et al., 2002, supra, found no differences in morphological development of *A. thaliana* plants expressing either *Arabidopsis* or *Parasponia* class 1 nsHb. Thus, our results were surprising in view of the work of Hunt.

The invention also provides a method for enhancing vegetative growth and yield under normal growing conditions. Generally, plants modified to over-express nsHb exhibit enhanced vegetative growth and yield under normal growing conditions as compared to non-transformed plants. Conversely, plants modified to under-express nsHb exhibit reduced vegetative growth and yield under normal growing conditions as compared to non-transformed plants. For example, nsHb+ plants exhibit increased yield per shoot.

Figure 4:
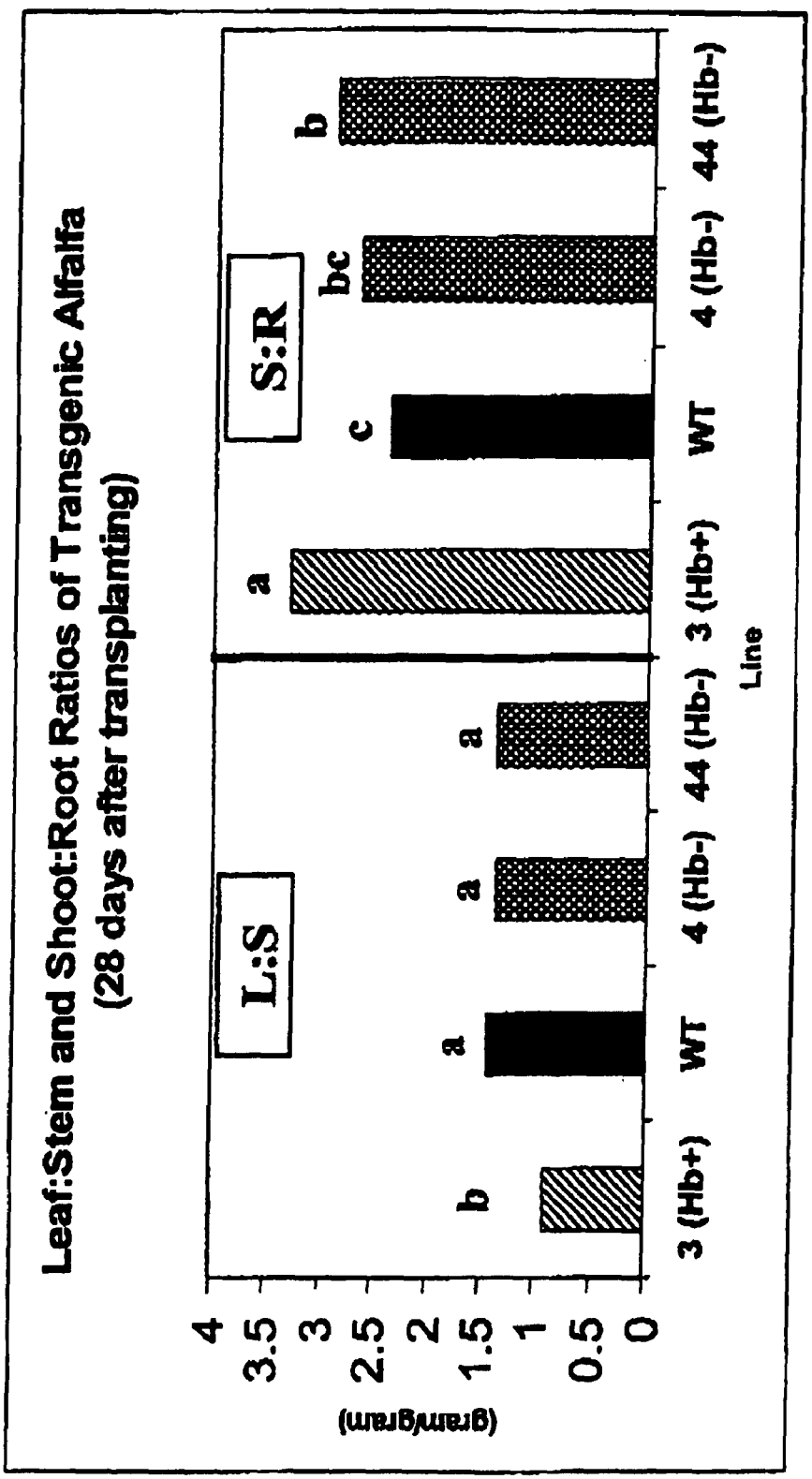
FIG. 4 is a bar graph of leaf:stem and shoot:root ratios of four transformed alfalfa plants at 28 days after transplantation.
Figure 5:
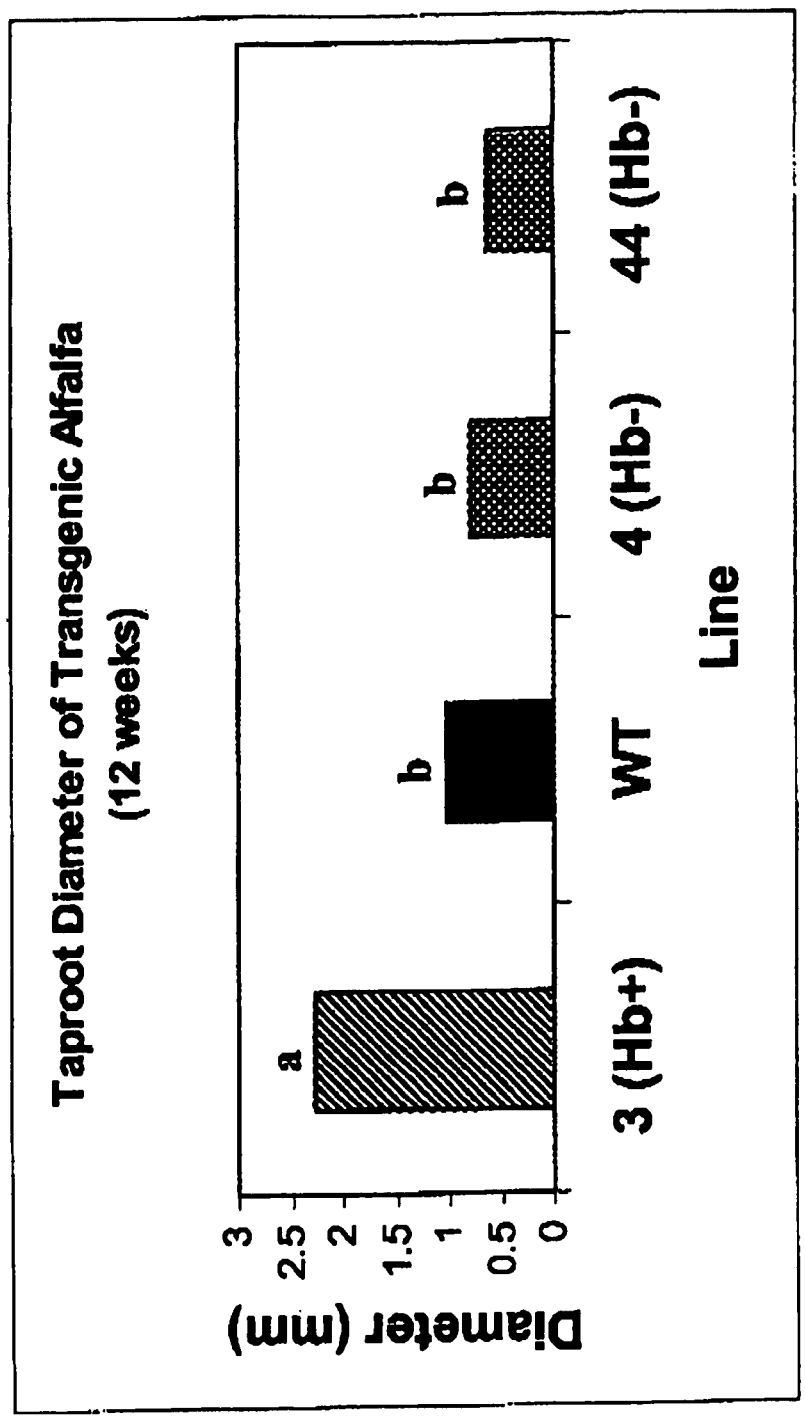
FIG. 5 is a bar graph of root morphology of four transformed alfalfa plants at 12 weeks after transplantation.
Figure 6:
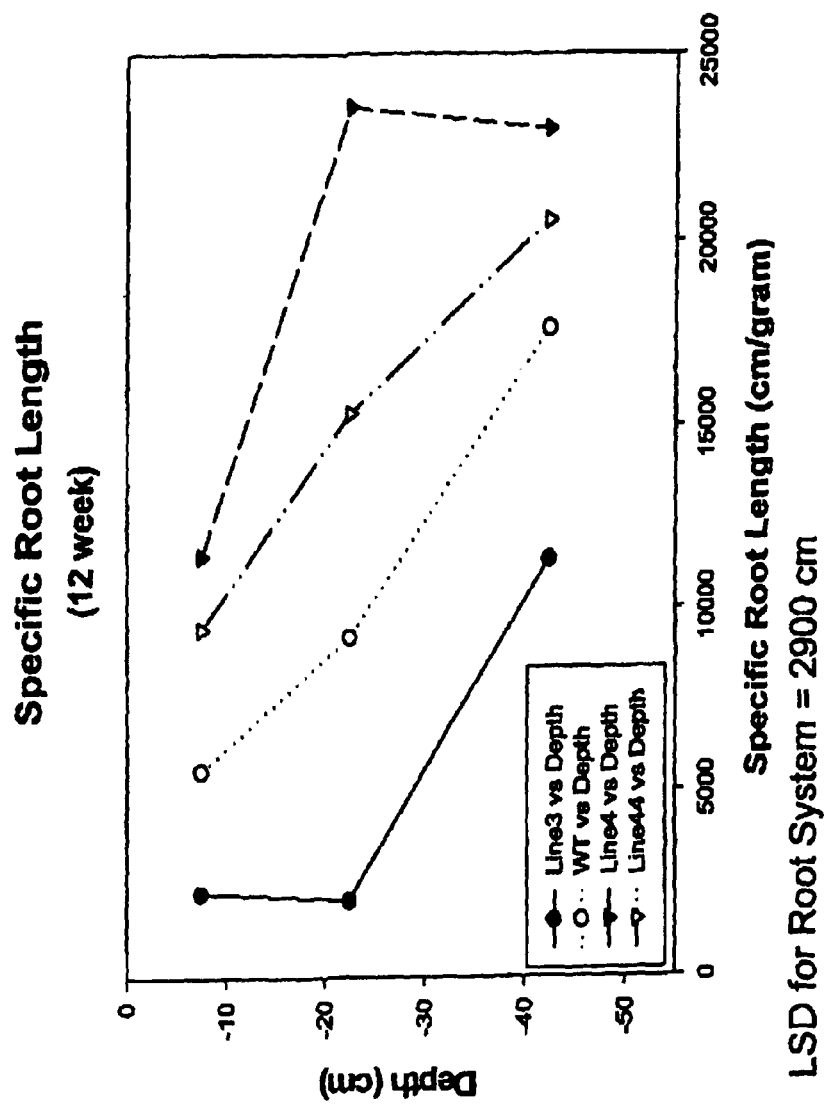
FIG. 6 is a comparative graph of depth versus specific root length for four transformed alfalfa plants at 12 weeks after transplantation.

The invention also contemplates methods for modifying the relative proportions of plant components, such as leaf, stem, and reproductive tissue, to enhance seed production or forage quality. Generally, plants modified to over-express nsHb exhibit an increased proportion of reproductive tissue. nsHb+ plants also may exhibit an increased shoot:root ratio and a lower leaf:stem ratio. See FIG. 4. nsHb− plants may exhibit decreased stem yield but increased leaf yield, and thus may exhibit an increased leaf:stem ratio. See FIG. 4.

While not wanting to be bound by any theory, the present inventors believe that the mechanism underlying the above-described changes in phenotype observed when a plant is modified to over-express or under-express nsHb in accordance with the invention, relates to changes in NO levels, which in turn affects hormone expression. The present invention therefore encompasses methods of modifying the effects of plant hormones, such as gibberellins, auxins, cytokinins, ABA and ethylene. In general, modifying a plant to over-express nsHb will decrease the effects of hormones that have NO as a component of the signal transduction pathway, while modifying a plant to under-express nsHb will increase the effects of these same hormones.

For example, the effects of nsHb over-expression on apical dominance and shoot:root ratios are consistent with an alteration of the auxin:cytokinin ratio; the effects on internode length, petiole length, petiolule length and leaf shapes consistent with an alteration of gibberellin response; the effect on the number of (trifoliate) leaves per node (with nsHb+ plants having fewer leaves per node) is consistent with an alteration of a cytokinin response; the effect on branching (with roots and shoots of nsHb− plants showing greater branching) is suggestive of an alteration of auxin:cytokinin ratios, and the effect on flower color also be an alteration of a hormonal response.

The invention also provides a method for modifying a plant's uptake, concentration, or metabolism of nutrients, such as mineral nutrients, from its growing environment, such as from the soil it is planted in. Generally, plants modified to under-express nsHb exhibit reduced uptake (and/or concentration) and/or metabolism of most nutrients (except Fe). Conversely, plants modified to over-express nsHb may exhibit increased uptake (and/or concentration) or metabolism of most nutrients (except Fe) as compared to non-transformed plants. Plants modified in accordance with the invention to exhibit increased nutrient uptake, concentration, or metabolism may be particularly useful for growing under poor soil conditions.

The inventors believe that the effect of nsHb on iron intake is reversed from most other nutrients, with iron uptake (or concentration) decreasing as nsHb expression increases. This is because of the effect of NO levels on Fe uptake, and the modulation of NO levels that is associated with nsHb expression. NO is believed to increase Fe uptake, while NO levels are inversely related to nsHb expression. Thus, the invention includes methods of modulating iron levels by altering expression of nsHb. In one embodiment, nsHb expression is suppressed to increase iron uptake or concentration in the plant.

In some plants, such as grass, it may be advantageous to modify one phenotype by over-expression of nsHb and one phenotype by under expression of nsHb. For example, grass shoots that under-express nsHb may have a prostrate growing habit that provides good ground coverage. On the other hand, grass roots that over-express nsHb may exhibit apical dominance such that they penetrate the earth more deeply and provide greater drought resistance (separate from the tolerance to hypoxic conditions attributable to nsHb expression itself, as described in WO 00/00597). The present invention provides a method of making a plant modified to express both advantageous phenotypes. Thus, in accordance with the present invention, the shoots of a plant may be modified to under-express nsHb while the roots of the plant are modified to over-express nsHb.

From the teachings provided herein, those skilled in the art will recognize other combinations of phenotypes for which it may be advantageous to have a plant with one or more phenotypes induced by nsHb− over-expression and one or more phenotypes induced by nsHb under expression.

Other modifications of plant phenotype achieved by the methods of the present invention are demonstrated in the examples set forth below.

EXAMPLES

Plant Material

Transgenic alfalfa (*Medicago sativa* cv. Regen SY) plants were generated from alfalfa root cultures containing sense and antisense orientation of barley nonsymbiotic hemoglobin as described in Dordas et al., 2003, *Plant J* 35: 763-70.

Transformation Vectors

Constructs containing the sense and antisense orientation of barley hemoglobin are obtained from pAS1 (containing sense) or pAS2 (containing antisense) plasmids. The fragment containing ubiquitin promoter+ubiquitin intron+hemoglobin+nos3' is inserted into the vector pWBVec8. The plasmids are used to transform *A. rhizogenesis* strain A4 using the freeze-thaw method. After transformation, incubation and amplification, plasmids are extracted from the bacteria and restriction enzyme-digested to verify transformation.

Alfalfa Transformation

Stem segments (2-cm long) are cut from alfalfa plants and placed inverted into Magenta boxes containing MSHF media. A loopful of *A. rhizogenes* A4 containing the appropriate constructs is placed on the exposed end of the explant. The control line (C) is transformed with an empty cassette. After a few weeks, one root from each stem segment is placed on a Petri plate with MSHF media containing 500 mg $l^{-1}$ carbenicillin and 20 mg $l^{-1}$ hygromycin. Each root is left to grow for few weeks and then screened at the DNA and protein levels for insertion of the hemoglobin gene and for quantification of the levels of expression of hemoglobin.

Generation of Alfalfa Plants from Alfalfa Root Cultures

Root segments (1 cm) of alfalfa root cultures are cut and placed on Petri Dishes containing SH induction media. After 3 to 4 weeks, root segments develop callus, after which calli are transferred to MSHF medium. Upon formation of somatic embryos, calli are subcultured every two weeks on MSHF medium. In approximately 3-4 months, embryos develop into plantlets. Plantlets are then transferred to magenta boxes containing sterile media and a peat:perlite (1:1) mixture. Following an acclimation period (4 weeks), plantlets are transferred to pots and placed under growth conditions described below.

Four lines were evaluated in these experiments: nsHb+ (3), Control (C), nsHb− (4) and nsHb− (44). All of the lines evaluated in these studies, including the empty vector control line (C), were generated in a single transformation experiment, as described above. The nsHb content of the four lines studied is shown is Table 1. There is almost ten-fold variation in the nsHb content between the lines having the highest and lowest nsHb content and the relative amounts are consistent with those of the root culture lines (Dordas et al., 2003, supra) from which the plants have been regenerated.

TABLE 1 nsHb content in the roots of transgenic alfalfa plants (35 DATP)

| Alfalfa Line | Hemoglobin Content (nmol g$^{-1}$ Fresh Weight) |
| --- | --- |
| Hb+ (3) | 12.042a ± 1.384 |
| Control | 4.061b ± .258 |
| Hb− (4) | 1.455c ± .046 |
| Hb− (44) | 1.359c ± .051 |

Plant Growth Conditions

Maintenance, rooting and growth studies of transgenic alfalfa plants, with the exception of root morphology studies, were conducted in growth chambers (Econaire-GR-36) set at day/night (22/19° C.; 16 h/8 h) with relative humidity maintained at 65-85%. Photosynthetic photon flux density within growth chambers ranged from 350 to 500 µmol m$^{-2}$ s$^{-1}$ at pot height. Cuttings of transgenic alfalfa plants were rooted for 20 d in root trainers filled with commercial growth medium (Terra-Lite, 2000; W.R. Grace & Co. Ajax, ON) prior to transplanting into 15-cm diameter pots containing a steam-sterilized sand:soil (2:1; v:v) mixture. Cuttings were initially transplanted at a density of 2 per pot and thinned to 1 per pot 7 days after transplanting ("DATP"). Pots were fertilized once a week with 1 g L$^{-1}$ of a commercial fertilizer (20-20-20, Plant Prod, Brampton, ON, Canada). Within the growth chamber, pots were assigned to quadrats centered about the point of highest light intensity and were rotated weekly to reduce variability in microclimate. Plants in shoot and root morphology experiments were kept well watered for the duration of the experiment(s).

For root morphology studies, stem cuttings (3 per pot) were transplanted into 55×20 cm PVC cylinders, placed in the greenhouse, and thinned to 1 per pot 14 DATP. Cylinders were lined with 2.5 cm of gravel and caps drilled to allow free drainage. Cylinders were then filled with soil mixture as previously described. Temperature was maintained at 25±5° C. for the duration of the experiment. Supplemental lighting was provided by 1000-W high-pressure sodium bulbs, set at 16-h photoperiod and supplying 600-1000 µmol mol m$^{-2}$s$^{-1}$ of light at pot height. PVC pots were re-randomized within the greenhouse at two-week intervals.

Harvest Protocols

Leaf, stem, and reproductive characteristics, along with total root and shoot dry weights of transgenic plants were monitored over 63 days of growth with harvests occurring 14, 21, 28, 35, and 63 DATP. For each harvest, shoots were clipped at the junction of the taproot and crown, placed in plastic bags, and held at 4° C. during the 2 days necessary for tissue separation. Shoot samples were separated into leaf, stem, and reproductive fractions. For leaf measurements (14, 21, 28 and 35 DATP) the number of leaves (leaflets plus petiolule) per stem (stem and petiole) was noted prior to leaf area determinations with a leaf area meter (LI-3100, LI-COR Inc., Lincoln, Nebr., USA). Plants were then separated into individual stems and staged according to the mean stage by count (MSC) method of Kalu and Fick (1981). Stems per plant, nodes per stem, and stem diameter at the centre of the lowermost internode were also recorded. Following shoot harvest, roots were submerged to remove excess rooting medium. Root systems were then placed on a fine screen and a stream of water directed through them. Between the 35 and 63 DATP harvest, time to flowering was noted. Racemes per plant and florets per raceme were recorded on the 72 DATP harvest. All tissues were dried at 70° C. for 48 hours prior to dry weight determinations. At 35 DATP, plants were analyzed for chlorophyll content according to Estill et al. (1991).

Root Morphology

For harvests occurring 63 and 84 DATP, cylinders were placed horizontally on a fine screen and rooting medium worked away under a stream of water. Following removal of debris, root systems were scored for taproot diameter (TD), lateral root number (LRN), lateral root position (LRP) and determinate taproot position (DTP) according to Johnson et al. (1998). Root systems were then separated into 0-15, 15-30, and 30-55 cm fractions, root lengths recorded using digitizing software (ASSESS software, APS Press), and dry weights determined.

Nutrient Analysis

For each transgenic line shoot tissue from the 35 DATP harvest and root tissue from 21-35 DATP harvests was ground on a Wiley Mill (1 mm) prior to being analyzed for mineral nutrient composition.

Experimental Design and Data Analysis

All experiments were analyzed as completely randomized designs. For shoot morphology and root morphology experiments six and three replicates were used respectively. Analysis of variance (SAS Institute, 1985) was used to partition variance into line and replicate effects. Where F-tests were significant, Fisher's protected LSD test (P≦0.05) was used for mean comparisons. Shoot morphology experiments were conducted three times (2× yield and morphology, 1× yield). Seedling root morphology experiments were conducted once while stem cutting root morphology experiments were conducted twice. Data from seedling root morphology experiments has been combined for ease of presentation.

Example 1

Phenotype, Growth, and Morphology of Transgenic Alfalfa

Transformation of alfalfa plants to over-express (Hb+) or under-express (Hb−) nsHb performed as described above resulted in the following phenotype modifications:

Flower Color

The modification of nsHb levels resulted in a change in flower color. The intensity of the purple color increased as nsHb expression declined.

Leaf Greenness & Chlorophyll Content

The modification of nsHb levels resulted in differences in leaf greenness and chlorophyll (chl) content, as shown in FIG. 2. Total chl content of nsHb+ plants was elevated relative to control plants whereas that of nsHb− plants was diminished.

Changes in total chl content and Chl a:b ratios in transgenic lines were brought about solely by changes in Chl b, and not Chl a.

Figure 1:
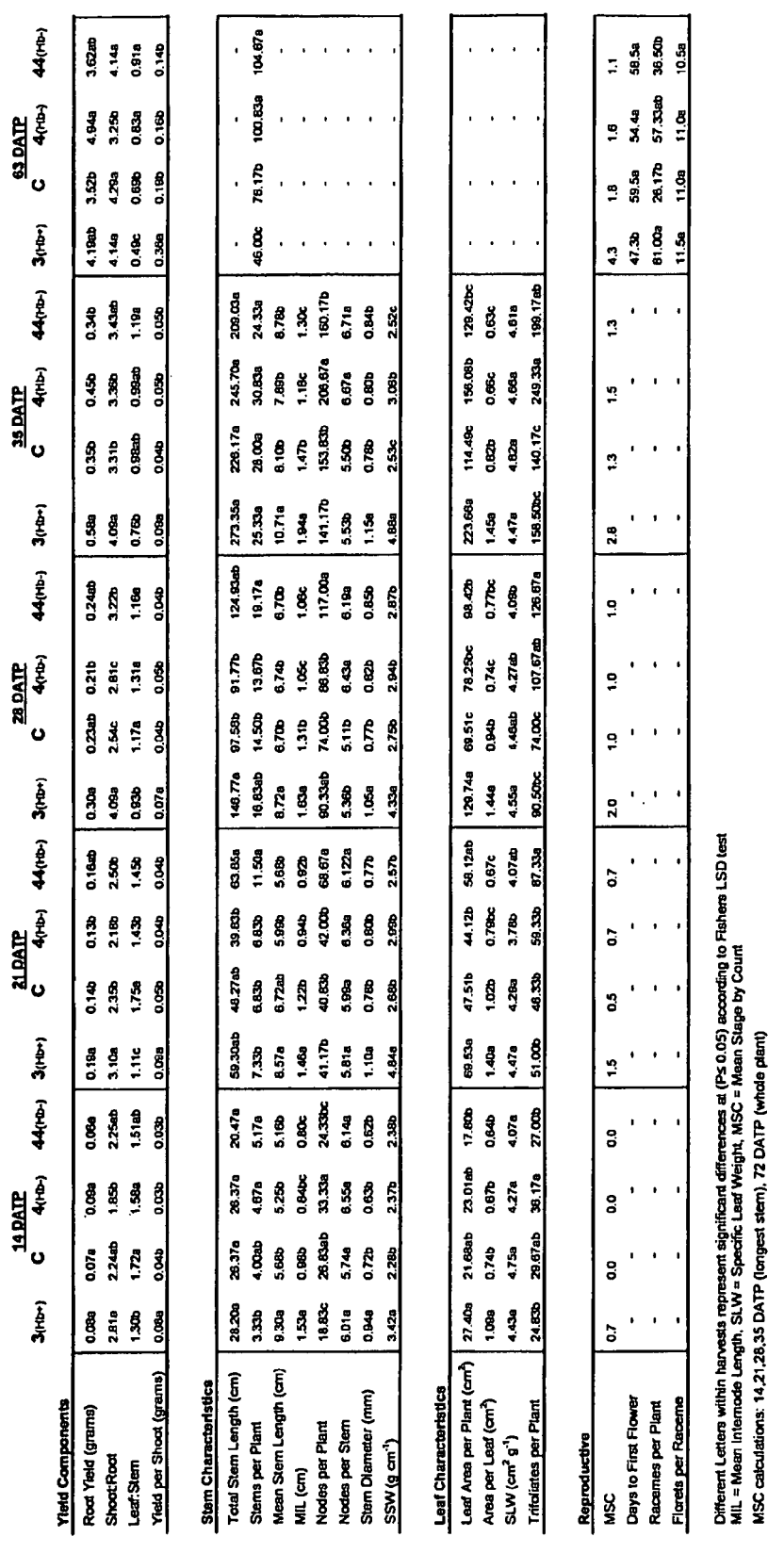

FIG. 1 sets forth additional data for the four plant lines at 14, 21, 28, 35 and 63 DATP, discussed below.

Yield, Stem, Leaf & Reproductive Characteristics

During early vegetative growth (14 to 35 DATP), nsHb+ plants produced 32-111% more shoot yield than control plants and produced significantly more shoot yield than all nsHb− plants across these same harvest dates. See FIG. 1 & FIG. 3. Adventitious root formation and resumption of shoot growth in nsHb lines in conjunction with high shoot to root ratios in nsHb+ lines led to non-significant differences in root yield of the transgenic lines at 14 DATP For harvests occurring 21, 28 and 35 DATP, root yield of nsHb+ plants tended to follow herbage yield exceeding both control and nsHb− plants (FIG. 1). However, root yield of nsHb+ plants was significantly greater (P≤0.05) than both control and nsHb− plants for the 35 DATP harvest only.

During vegetative growth, the shoot:root ratio of nsHb+ plants always exceeded that of control and nsHb− plants (FIG. 1). For all lines, the shoot:root ratio was observed to increase with successive harvests between 14 and 35 DATP (FIG. 1). For the 28 DATP harvest nsHb− (44) plants, which had slightly higher shoot yields (FIG. 3), also demonstrated elevated shoot:root ratios relative to control and nsHb− (4) plants (FIG. 1).

At the 63 DATP harvest, as was the case for harvests 14, 21, 28, and 35 DATP, nsHb+ plants consistently demonstrated a lower leaf:stem ratio than control and nsHb− plants (FIG. 1). The leaf:stem ratio of control and nsHb− plants did not significantly differ during vegetative growth except at 21 DATP where the leaf:stem ratio of control plants exceeded that of both nsHb+ and nsHb− plants (FIG. 1). At 63 DATP, the leaf:stem ratio of nsHb+ plants was significantly reduced, and that of nsHb− plants significantly elevated, relative to control plants (FIG. 1).

For all harvest dates, yield per shoot (YPS) of nsHb+ plants exceeded that of control and nsHb− plants with no significant differences observed between control and nsHb− plants across all harvest dates (FIG. 1).

Figure 3:
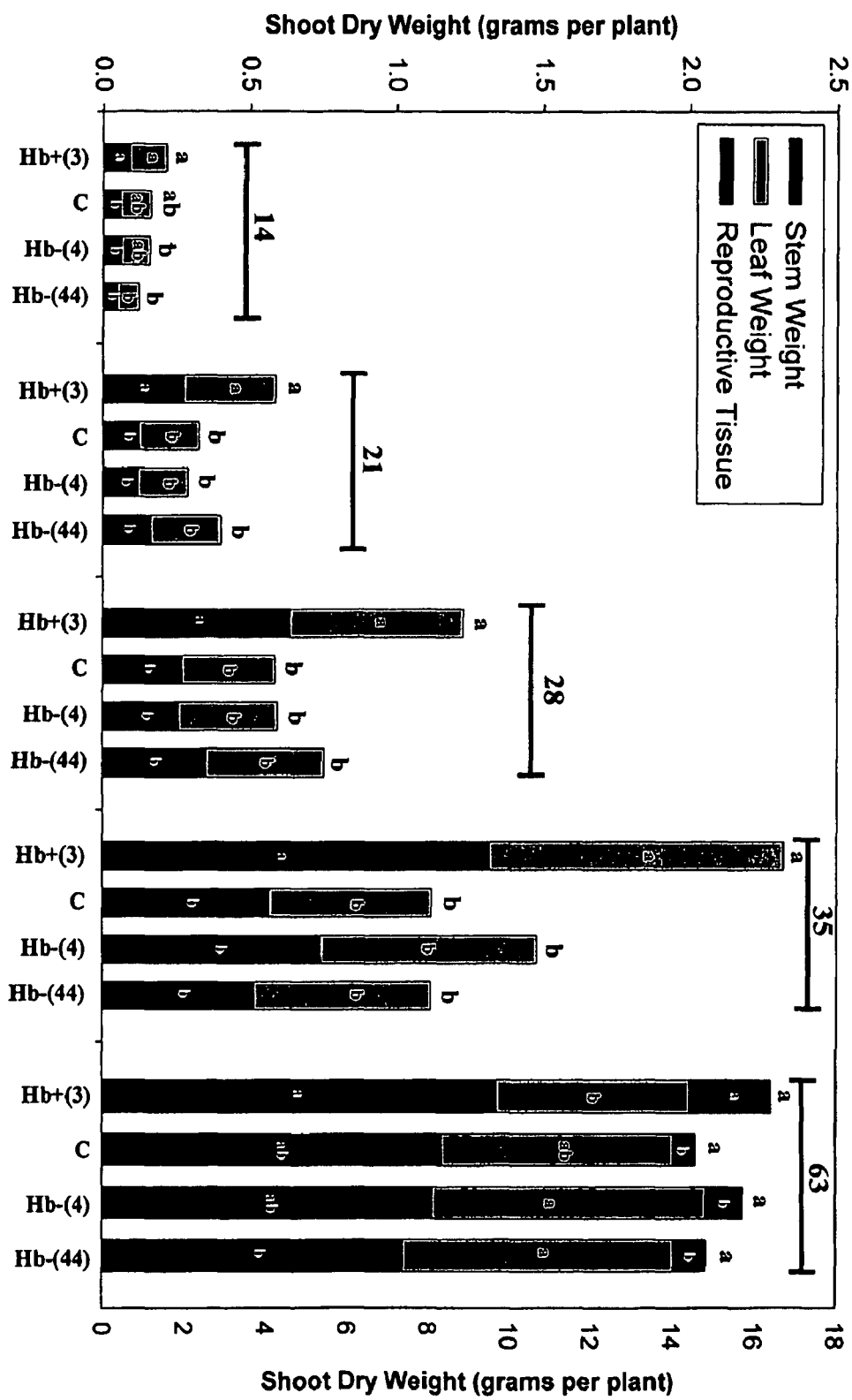
FIG. 3 shows the stem weight, leaf weight, reproductive tissue weight and shoot dry weight for four transformed alfalfa plants at 14, 21, 28, 35 and 63 days after transplantation.

Stem weight of nsHb+ plants exceeded all other lines during vegetative growth. See FIG. 3. For these same harvest dates, leaf weight displayed a similar pattern to that of stem weight, except for the 14 DATP harvest where nsHb+ plants exceeded only nsHb− (44) plants for leaf weight. See FIG. 3. Leaf weight of control and nsHb− (4) plants was intermediate to that of nsHb+ and nsHb− (44) plants 14 DATP (FIG. 3). At the 63 DATP harvest, total shoot yield (leaf+stem+reproductive) was not significantly different between transgenic plants. However, nsHb+ plants were noted to flower sooner (see FIG. 1) and produce more reproductive tissue than control or nsHb− plants (see FIG. 3). At this same harvest date, stem yield was observed to decrease, and leaf yield increase, as nsHb expression declined. See FIG. 3. Similar results for shoot DW, in addition to significant differences in the FW:DW ratio in the shoots of transgenic lines, were observed in subsequent experiments, as shown in Table 2.

TABLE 2

| | Shoot Dry Weight (g) DATP | | | |
| --- | --- | --- | --- | --- |
| | 14 | 21 | 28 | 35 |
| Hb+ (3) | 0.24a ± .02 | 0.51a ± .01 | 1.22a ± .05 | 2.19a ± .18 |
| WT | 0.18b ± .01 | 0.38ab ± .03 | 0.56b ± .04 | 1.05b ± .03 |
| Hb− (4) | 0.17b ± .01 | 0.36b ± .04 | 0.77b ± .04 | 1.38b ± .11 |
| Hb− (44) | 0.13b ± .01 | 0.31b ± .02 | 0.63b ± .09 | 0.89b ± .04 |

TABLE 2-continued

| | Fresh Weight (g):Dry Weight (g) DATP | |
| --- | --- | --- |
| | 14 | 21 |
| Hb+ (3) | 4.24b ± .08 | 3.78c ± .08 |
| WT | 4.16b ± .07 | 4.03b ± .06 |
| Hb− (4) | 4.70a ± .22 | 4.78a ± .09 |
| Hb− (44) | 4.77a ± .07 | 4.74a ± .08 |

Table 2 shows shoot yield and fresh weight:dry weight ratios of transgenic alfalfa plants expressing varying levels of a class 1 nonsymbiotic barley hemoglobin. Different letters within harvest dates represent significant differences according to Fisher's protected LSD (P≤0.05). Harvest dates expressed in DATP (days after transplanting).

Despite relatively few significant differences in the shoot and root yield of control and nsHb− plants, a number of morphological parameters distinguished these plants from one another in addition to nsHb+ plants. During vegetative growth the mean internode length and area per leaflet was increased in nsHb+ plants relative to control plants (FIG. 1). In contrast, nsHb− plants experienced reductions in both of these parameters relative to control plants (FIG. 1). In the case of nsHb− plants, impaired stem elongation and leaflet expansion resulted in production of greater numbers of stems per plant, nodes per stem and leaflets per plant (FIG. 1). Although nsHb+ plants produced stem numbers equal to or less than control and nsHb− plants, stems produced were consistently thicker and had elevated specific stem weights (SSW) relative to control and nsHb− plants (FIG. 1). nsHb+ plants also produced elongated and needled leaflets with longer petioles and petiolules. In comparison, nsHb− plants produced compressed oval leaflets with shortened petioles and petiolules.

Staging transgenic plants according to the MSC method of Kalu and Fick (1981) suggested nsHb+ plants to have accelerated morphological development relative to control and nsHb− plants at all harvest dates (FIG. 1). At 63 DATP, morphological development according to the MSC method placed nsHb− plants behind control plants. However, at this time point nsHb− plants had more stems in the early (5) to late flower (6) stages than comparable control plants (data not shown), and lower MSC rankings were attributed to an extremely high number of stems in the early vegetative (0) stage. Greater weight of reproductive tissue and racemes per plant for nsHb− plants relative to control plants, although not significant, lend support to such observation (FIG. 1). As several nsHb+ plants contained stems in the late flower (6) and early seed pod (7) stages at 63 DATP, petal drop was suspected in having led to underestimation of reproductive tissue in this line.

Root Morphology

Rooted stem cuttings and seedling root systems of transgenic alfalfa plants displayed a number of morphological characteristics which distinguished such plants from one another. nsHb expression appeared to influence the time required for cuttings to root, in addition to the number of adventitious roots forming on such cuttings. Cuttings of nsHb− and control plants rooted sooner than comparable cuttings from nsHb+ plants. nsHb− plants were observed to produce significantly more adventitious roots than nsHb+ or control plants 15 and 20 days after placing cuttings into rooting medium.

Table 3 sets forth data on shoot weight and root weight and characteristics for the four plant lines at 14, 21, 28, 35 and 63 DATP.

TABLE 3

| Line | Shoot Weight (grams) | Root Weight (grams) | MSC | TL (cm) | TD | DTP score | LRN score | LRP score |
|---|---|---|---|---|---|---|---|---|
| Hb+ (3) | 3.63 | 0.65 | 1.97 | 63.10 | 4.83 | 0.17 | 1.50 | 2.83 |
| C | 2.45 | 0.26 | 0.31 | 65.08 | 3.17 | 1.00 | 1.67 | 3.33 |
| Hb− (4) | 2.42 | 0.17 | 0.14 | 52.22 | 2.33 | 2.00 | 2.00 | 5.00 |
| Hb− (44) | 2.13 | 0.17 | 0.22 | 45.50 | 1.67 | 2.67 | 2.33 | 5.00 |
| $LSD_{(0.05)}$ | 1.41 | 0.31 | — | 16.97 | 0.68 | 1.15 | 0.77 | 1.57 |
| CV (%) | 43.93 | 81.39 | — | 24.95 | 18.75 | 65.34 | 34.08 | 32.33 |

When compared to control plants, roots of nsHb+ seedlings rapidly grew to the bottom of PVC pots and produced thicker, but not longer, taproots. (Table 3). In contrast, nsHb− plants allocated the majority of their root weight and root length to the upper portion of the soil strata, producing thin taproots slightly shorter than observed for control plants (Table 2). Non-significant differences in taproot length between lines were attributed to root growth of control and nsHb− lines along the soil-PVC interface and nsHb+ plants having reached the bottom of cylinders by 63 DATP.

Determinate taproot position (DTP) was used to gauge apical dominance of taproots below the crown of transgenic alfalfa plants. DTP score decreased with nsHb expression suggesting apical dominance of taproots to be lost as nsHb expression declined (Table 3). nsHb+ plants produced significantly fewer lateral roots than nsHb− (44) plants only, with control and nsHb−(4) plants falling intermediate (Table 3). Scoring transgenic plants for lateral root position (LRP), the lateral root closest to the crown, suggested nsHb− plants to position lateral roots closer to the crown than control and nsHb+ plants (Table 3). The differences in taproot diameter (Table 3) and fibrous root mass observed between root systems also resulted in significant differences in the specific root length (SRL) of transgenic lines. For all lines, SRL increased with soil depth. SRL of nsHb+ plants exceeded that of control plants, which in turn, exceeded nsHb− plants.

A notable characteristic of nsHb+ plants was an abundance of hypertrophied lenticels upon both taproots and lateral roots.

Nutrient Uptake

Table 4 shows the mineral nutrient concentration in the shoots of the transformed alfalfa plants harvested 35 DATP (Days After Transplanting).

TABLE 4

| | Shoots | | | |
|---|---|---|---|---|
| Nutrient | Hb+(3) | C | Hb−(4) | Hb−(44) |
| N | 3.48a ± .13 | 3.43a ± .11 | 2.78b ± .13 | 2.60b ± .12 |
| P | 0.25d ± .005 | 0.31b ± .006 | 0.28c ± .004 | 0.33a ± .007 |
| K | 2.58a ± .06 | 1.98b ± .03 | 1.95b ± 0.03 | 1.88b ± .03 |
| S | 0.330a ± .01 | 0.303a ± .01 | 0.230b ± .01 | 0.318a ± .02 |
| Ca | 2.033b ± .05 | 3.235a ± .06 | 3.008a ± .12 | 3.163a ± .25 |
| Mg | 0.583b ± .01 | 0.953a ± .02 | 0.908a ± .04 | 0.940a ± .05 |
| Na | 0.033c ± .003 | 0.035bc ± .003 | 0.048b ± .003 | 0.040b ± .003 |
| Zn | 15.75b ± .48 | 23.75a ± 3.77 | 19ab ± .41 | 20.75ab ± .95 |
| Fe | 99.5a ± 9.79 | 103.25a ± 3.12 | 112.25a ± 10.42 | 155.5a ± 50.47 |
| Mn | 95.25c ± 4.03 | 164.25b ± 4.80 | 149.75b ± 24.42 | 258.75a ± 24.49 |
| Cu | 10.5c ± .29 | 17.75b ± .25 | 18.25b ± 1.44 | 21.25a ± .75 |
| B | 65.5c ± 1.85 | 97.25ab ± 1.60 | 90.5b ± 3.80 | 109a ± 8.22 |

The nutrient analysis for Nitrogen (N), Phosphorus (P), Potassium (K), Sulphur (S), Calcium (Ca), Magnesium (Mg) and Sodium (Na) is expressed on a % dry matter basis. The nutrient analysis for Zinc (Zn), Iron (Fe), Manganese (Mg), Copper (Cu), and Boron (B) is expressed in parts per million (ppm). The different letters (a, b, c, d) listed in the amounts represent significant differences according to Fisher's Protected LSD ($P \leq 0.05$).

Unless defined otherwise, all technical and scientific terms used herein have the same meaning as commonly understood by one of ordinary skill in the art to which the invention belongs.

While specific embodiments of the invention have been described above, it will be recognized and understood that various modifications may be made therein, and the appended claims are intended to cover all such modifications which may fall within the spirit and scope of the invention.

What is claimed is:

1. A method of obtaining a plant exhibiting a modified phenotype, comprising:
    growing, under non-hypoxic conditions, a plant that comprises an expression vector comprising a nucleotide sequence encoding a plant non-symbiotic hemoglobin in an antisense orientation, thereby yielding a plant having a reduced level of expression of non-symbiotic plant hemoglobin as compared to a control plant that does not comprise said expression vector, and
    selecting a plant exhibiting a plant phenotype that is modified as compared to said control plant, wherein said phenotype is selected from the group consisting of shoot or root apical dominance; flower color; shoot branching; and chlorophyll content.

2. The method of claim 1, wherein said expression vector comprises a repressible promoter that permits selective repression of expression of a plant non-symbiotic hemoglobin.

3. The method of claim 1, wherein the selected plant exhibits increased flower pigmentation compared to the control plant.

4. The method of claim 1, wherein the selected plant exhibits decreased chlorophyll content compared to the control plant.

5. The method of claim 1, wherein the selected plant exhibits decreased root apical dominance compared to the control plant.

6. The method of claim 1, wherein the selected plant exhibits increased shoot branching compared to the control plant.

7. A method of obtaining a plant exhibiting a modified phenotype, comprising:
    selecting a plant that comprises an expression vector comprising a nucleotide sequence encoding a plant non-symbiotic hemoglobin in antisense orientation, thereby having a reduced level of expression of non-symbiotic plant hemoglobin as compared to a control plant that does not comprise said expression vector, and that has been grown under non-hypoxic conditions, wherein said selected plant exhibits a plant phenotype that is modified as compared to said control plant, wherein said phenotype is selected from the group consisting of shoot or root apical dominance; shoot branching; flower color; and chlorophyll content.

* * * * *